United States Patent [19]

Slaugh

[11] Patent Number: 5,008,480

[45] Date of Patent: Apr. 16, 1991

[54] PROCESS FOR CONVERTING TOLUENE AND BUTADIENE TO STYRENE AND 1-PENTENE

[75] Inventor: Lynn H. Slaugh, Cypress, Tex.

[73] Assignee: Shell Oil Company, Houston, Tex.

[21] Appl. No.: 484,299

[22] Filed: Feb. 26, 1990

[51] Int. Cl.$^5$ ............................ C07C 1/00; C07C 4/24; C07C 5/23

[52] U.S. Cl. .................................. 585/323; 585/439; 585/474; 585/452; 585/664; 585/435

[58] Field of Search .............. 585/323, 439, 474, 452, 585/664, 435

[56] References Cited

U.S. PATENT DOCUMENTS 3,261,879  9/1963  Banks .
3,365,513  1/1968  Heckelsberg .

FOREIGN PATENT DOCUMENTS 1054864  1/1967  United Kingdom .
1338429  11/1973  United Kingdom .

OTHER PUBLICATIONS

Dunning "Review of Olefin Isomerization" Ind. Eng. Chem. (45) 551-564 (1953).

*Primary Examiner*—W. J. Shine
*Assistant Examiner*—J. Saba

[57] ABSTRACT

The instant invention relates to a process for converting toluene and butadiene to styrene and 1-pentene by:

(a) reacting touene and 1,3-butadiene in the presence of an alkali metal catalyst, (b) contacting the butenylated reaction product of step (a) with a double bond isomerization catalyst at a temperature sufficient to cause double isomerization, (c) reacting the isomerized product of step (b) with ethylene in the presence of a disproportionation catalyst, and (d) separating from the reaction product of step (c) product styrene and 1-pentene.

7 Claims, No Drawings

PROCESS FOR CONVERTING TOLUENE AND BUTADIENE TO STYRENE AND 1-PENTENE

FIELD OF THE INVENTION

This invention relates to a process for converting toluene and butadiene to styrene and 1-pentene.

BACKGROUND OF THE INVENTION

Butadiene is a commodity chemical, which, because of economic cycles, can be at times in surplus. When it is in surplus, it is desirable to convert it to higher value products. Styrene is a valued chemical which finds many uses, such as being used as a component in styrenic polymers. Coproduct 1-pentene can be used as a feedstock to prepare specialty detergents or lube stocks.

SUMMARY OF THE INVENTION

The instant invention relates to a process for converting toluene and butadiene to styrene and 1-pentene, which process comprises:
(a) reacting toluene and 1,3-butadiene in the presence of an alkali metal catalyst at a temperature ranging from about 0° C. to about 150° C., thereby producing a butenylated reaction product,
(b) contacting the butenylated reaction product of step (a) with a double bond isomerization catalyst at a temperature ranging from about 50° C. to about 200° C., thereby producing an isomerized reaction product,
(c) reacting the isomerized reaction product of step (b) with ethylene in the presence of a disproportionation catalyst at a temperature ranging from about −10° C. to about 100° C., thereby producing a disproportionated reaction product, and
(d) separating from the resulting product of step (c) product styrene and 1-pentene.

DETAILED DESCRIPTION OF THE INVENTION

The first step of the instant process is to react toluene with 1,3-butadiene in the presence of a metallic alkali metal catalyst. While any of the Group IA metals can be utilized as a catalyst, sodium and potassium are preferred. The alkali metal catalyst can be utilized as such in a dispersed form in the reaction medium or, preferably, it is supported on a nonacidic oxide support. Group IA and Group IIA oxides are typically utilized as supports and preferably calcium oxide and sodium oxide are utilized. Alumina also provides a suitable support. Mixed metallic alkali metals can be utilized, such as a sodium-potassium mixture supported on calcium oxide.

The butenylation reaction is carried out at temperatures ranging from about 0° C. to about 150° C. and preferably from about 25° C. to about 130° C. Reaction pressures are not critical and will typically range from about atmospheric to about 100 bars.

The butenylation reaction may be carried out in a batch reactor or in a continuous flow reactor. For example, it may be carried out in a traditional fixed bed reactor, the bed comprising a supported metallic alkali metal catalyst, wherein toluene and butadiene in a cocurrent or counter current flow mode is passed over the bed to carry out the reaction. Trickle phase and continuous stirred tank reactors are also suitable. Other continuous reactor configurations will be readily apparent to one skilled in the art.

Batch reactors, such as autoclaves, are also suitable. For example, reactant toluene and catalyst are charged to an autoclave which is then pressured with butadiene and heated to the reaction temperature to allow the reaction to be carried out. Alternatively, reactant toluene and catalyst are charged to a stirred tank reactor and butadiene is bubbled through the reaction at reaction temperature in order to carry out the reaction.

To avoid multiple butenylated products the molar ratio or reactant toluene to butadiene is kept at greater than one. Batch reactions utilizing an excess of toluene in conjunction with a controlled addition of the butadiene yield a monobutenylated product exclusively.

After reaction is complete, the reaction mixture can be treated to remove any remaining catalyst by well known means, such as filtration, with or without decomposition of the catalyst, flash distillation, etc. At this point, butenylated reaction product can be separated from the reaction mixture by traditional means such as distillation or fractional crystallization and the butenylated toluene passed on to the second, or isomerization step of the instant process. Alternatively, the reaction mixture can be flashed to remove unreacted butadiene, and the resulting product passed on to the isomerization step.

The major product of the butenylation reaction will be 5-phenyl-2-pentene.

The second step of the instant process comprises isomerizing the butenylated reaction product of the first step by contact with a double bond isomerization catalyst at isomerization conditions. The double bond isomerization catalysts that are employed in the second step are any of the well known isomerization catalysts which promote double bond isomerization with little or no concurrent polymerization or cracking. Suitable examples are exemplified as phosphoric acid, both supported and unsupported, bauxite, alumina supported cobalt oxide, or iron oxide or manganese oxide, alkali metals such as sodium and potassium on an inert carrier materials such as alumina, alkali metal promoted aluminas such potassium carbonate on alumina, supported platinum group metals, magnesium oxide, calcium oxide, metal hydrides, organoalkali compounds, metal hydroxides and the like. Other suitable isomerization catalysts are disclosed in the publications "Review of Olefin Isomerization", H. N. Dunning, *Industrial and Engineering Chemistry*, 45, 551–564 (1953) and "Base-Catalyzed Reactions of Hydrocarbons and Related Compounds", edited by H. Pines and W. M. Stalich, Academic Press, 1977, pp.25–51. Particularly suitable catalysts are the alkali metal carbonate promoted aluminas, such as those prepared by impregnating a porous alumina support with a solution of an alkali metal carbonate, such as potassium carbonate, drying and calcining under a flow of nitrogen at elevated temperatures, say, 575° C. for about fourteen hours.

The isomerization reaction is carried out temperatures ranging from about 50° C. to about 200° C., preferably from about 75° C. to about 175° C., and more preferably from about 100° C. to about 150° C. Reaction pressures are not critical and will typically range from about atmospheric to about 100 bars.

The isomerization reaction may be carried out in a batch reactor or in a continuous flow reactor. For example, it may be carried out in a traditional fixed bed reactor, the bed comprising a supported metallic alkali metal catalyst, wherein the butenylated product from the first reaction is passed over the bed to carry out the reaction. Trickle phase and continuous stirred tank reactors are also suitable. Other continuous reactor configurations will be readily apparent to one skilled in the art.

Batch reactors, such as autoclaves, are also suitable. For example, the butenylated product reactant toluene and catalyst are charged to an autoclave which is then heated to the reaction temperature to allow the isomerization reaction to be carried out.

After the isomerization reaction is complete, the reaction mixture can be treated to remove any remaining catalyst by well known means, such as filtration, with or without decomposition of the catalyst, flash distillation, etc. At this point, the isomerized reaction product can be separated from the reaction mixture by traditional means such as distillation crystallization and passed on to the third or ethenolysis step of the instant process. Non-isomerized 5-phenyl-2-butene can be recycled to the isomerization step.

The major product of the isomerization reaction will be 1-phenyl-1-pentene.

The third step of the instant process comprises reacting the isomerized reaction product of the second step with ethylene in the presence of a disproportionation catalyst. The disproportionation catalysts employed in the third step of the instant process are also known in the prior art. Any solid catalyst system which is capable of promoting or catalyzing the olefin disproportionation reaction of butene-2 and ethylene to propylene is suitable. Preferably the disproportionation catalyst is one of molybdenum, tungsten and/or rhenium oxide supported on a refractory oxide support, preferably alumina. U.S. Pat. No. 3,261,879 discloses a molybdenum oxide-promoted catalyst. U.S. Pat. No. 3,365,513 discloses a tungsten oxide-promoted catalyst. A rhenium oxide-promoted catalyst is disclosed in British Patent 1,054,864. A rhenium oxide, molybdenum and/or tungsten oxide-promoted catalyst is disclosed in British patent 1,338,429. As reported in the prior art, these solid catalysts can also contain minor amounts of various treating agents, such trialkylaluminum compounds, dialkylaluminum halides, mono- and polyvalent alcohols, and the like. It is also sometimes advantageous to treat the solid catalyst with suitable gases, such as carbon dioxide, hydrogen and the like. The disproportionation catalysts can also be treated with the alkaline earth and alkali metal compounds as reported in the prior art. Preferably, a compound of sodium or potassium is used. Rhenium catalysts have also been promoted with tin compounds, such as tin oxide. Tetraalkyl tin compounds have also been utilized as promoters. The tetraalkyl tin compounds (alkyl being lower alkyl of $C_1$–$C_8$) are added to the reaction mixture to increase the activity of the rhenium catalyst. Tetramethyl tin, tetraethyl tin, tetrapropyl tin and tetrabutyl tin compounds are frequently utilized. An alumina supported rhenium catalyst promoted by tetraalkyl tin, preferably tetrabutyl tin, is a preferred catalyst for the ethenolysis reaction.

The ethenolysis reaction is carried out at temperatures ranging from about $-10°$ C. to about $100°$ C., preferably from about $0°$ C. to about $80°$ C., more preferably from about $20°$ C. to about $50°$ C. Reaction pressures are not critical and will typically range from about atmospheric to about 100 bars.

The ethenolysis reaction may be carried out in a batch reactor or in a continuous flow reactor. For example, it may be carried out in a traditional fixed bed reactor, the bed comprising the supported disproportionation catalyst, wherein the isomerized product from the isomerization reaction and ethylene in a cocurrent or counter current flow mode is passed over the bed to carry out the reaction. Trickle phase and continuous stirred tank reactors are also suitable. Other continuous reactor configurations will be readily apparent to one skilled in the art.

Batch reactors, such as autoclaves, are also suitable. For example, isomerized product from the isomerization reaction and catalyst are charged to an autoclave which is then pressured with ethylene and heated to the reaction temperature to allow the reaction to be carried out. Alternatively, isomerized product from the isomerization reaction and catalyst are charged to a stirred tank reactor and ethylene is bubbled through the reaction at reaction temperature in order to carry out the reaction.

After reaction is complete, the reaction mixture can be treated to remove any remaining catalyst by well known means, such as filtration or centrifugation. At this point styrene and 1-pentene can be separated from the reaction mixture by traditional means. For example, flash distillation can be used to remove the 1-pentene and ethylene, followed by further distillation to separate pentene and ethylene, and fractional distillation can be used separate out the styrene.

Inert solvents such as alkanes, e.g., cyclohexane, dodecane, hexadecane, octane, nonane, etc., can be utilized in either or all of the butenylation, isomerization or ethenolysis steps.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

The invention will be described by the following examples which are provided for illustrative purposes and are not to be construed as limiting the invention.

Illustrative Embodiment I

A. Butenylation Reaction Catalyst Preparation:

Finely powdered calcium oxide was heated in a quartz tube to $575°$ C. under a flow of dry nitrogen (200 ml/min). The freshly calcined calcium oxide (50 g) was placed in a 500 ml single neck Morton flask with 1.5 g of sodium metal chips under a nitrogen atmosphere. The mixture was heated to about $200$–$240°$ C. and tumbled on a rotary evaporator for 3 hours under an argon atmosphere to give a uniform grey-purple powder.

Reaction

The freshly prepared sodium on calcium oxide catalyst (50 g) was placed under a nitrogen atmosphere in a 500 ml three necked flask equipped with an air stirrer, reflux condenser, thermometer, gas inlet tube for the introduction of nitrogen and 1,3-butadiene and a gas outlet tube. Dry toluene (185 g, 2.0 mole) was added to the catalyst and the mixture was stirred and heated to $90°$–$95°$ C. under a nitrogen blanket. Butadiene (49 g, 0.91 mole) was bubbled through the stirred mixture over a period of 7 hours at $90°$–$95°$ C.

The reaction mixture was cooled to 20° C. and the catalyst was destroyed by the slow addition of isopropyl alcohol. The reaction mixture was filtered through a celite pad and the solids were washed with toluene. The toluene wash and filtrates were combined and washed with deionized water until neutral and then dried over magnesium sulfate. Filtration followed by distillation via a 6" vigeroux column yielded 28.3 g (10% yield based on conversion of toluene and 22% yield based on conversion of butadiene) of a colorless oil (b.p. 199°-21° C.). Analysis by gas chromatography, GC/MS and $^{13}C$ NMR showed the product to be 94% 5-phenyl-2-pentene (mixture of cis and trans isomers), 4% 5-phenyl-1-pentene and less than 1% 1-phenyl-1pentene.

B. Isomerization Reaction

Catalyst

The catalyst was a 15% $K_2CO_3$/alumina which was prepared by impregnating alumina (Kaiser KA-201 alumina) with a aqueous potassium carbonate solution, drying and calcining at 120° C. for 14 hours, followed by activation in nitrogen at 575° C. for 14 hours.

Reaction

A 100 ml stirred Parr autoclave was charged with a nitrogen purged solution of 29.0 grams of 5-phenyl-2-pentene from the above butenylation reaction in 35 ml of dry hexadecane and 10 grams of activated 15%$K_2CO_3$/alumina. The autoclave was sealed, stirred at 120°-130° C. for 5.5 hours, cooled to 20° C. and the catalyst was filtered off. Analysis of the filtrate by GC/MS and $^{13}$ NMR the product to be 63% 1-phenyl-1-pentene (68% isomerization), 30% 5-phenyl-2-pentene and 1% 5-phenyl-1-pentene.

C. Ethenolysis Reaction

Catalyst

The catalyst was a 15% $Re_2O_7$/alumina material which had been activated by heating at 540° C. for 2.5 hours under an air flow of 20 1/hr followed by heating at 540° C. under a nitrogen flow of 20 1/hr for 1.5 hours.

Reaction

To a nitrogen-purged 100 ml hoke addition vessel was added a nitrogen-purged solution of about 28 grams of the product mixture of the isomerization step containing 63% 1-phenyl-1-pentene and 30% 5-phenyl-2-pentene, 35 ml of dry nitrogen-purged hexadecane and 1.6 ml (5 mmole) of tetrabutyl tin under a nitrogen atmosphere. To a 100 ml Parr autoclave, under a nitrogen atmosphere, was added 6.0 g (5 mmole of rhenium) of the activated rhenium oxide/alumina catalyst. The hoke addition vessel was affixed to the Parr autoclave and the contents of the hoke vessel were pressured into the autoclave with 500 psi of ethylene at room temperature. The reaction mixture was stirred for 16 hours under 500 psi ethylene pressure, cooled to 5° C. and then the gas pressure was vented off through a gas sample vessel. Analysis of gas sample by GC/MS verified that the only two significant ethenolysis products obtained were propylene (from ethenolysis of 5-phenyl-2-pentene) and 1-pentene (from ethenolysis of 1-phenyl-1-pentene). Propylene could have been eliminated had the non-isomerized 5-phenyl-2-pentene been separated out prior to ethenolysis. Analysis of the liquid fraction of the reaction mixture by GS/MS, gas chromatography and $^{13}C$ NMR established a 95% conversion of the 1-phenyl-1-pentene to styrene.

What is claimed is:

1. A process for converting toluene and butadiene to styrene and 1-pentene, which process comprises:
   (a) reacting toluene and 1,3-butadiene in the presence of an alkali metal catalyst,
   (b) contacting the reaction product of step (a) with a double bond isomerization catalyst at a temperature sufficient to effect double bond isomerization,
   (c) reacting the isomerized product of step (b) with ethylene in the presence of a disproportionation catalyst, and
   (d) separating from the resulting product of step (c) product styrene and 1-pentene.

2. The process of claim 1 wherein step (a) is carried out at a temperature ranging from about 0° C. to about 150° C., step (b) is carried out a temperature ranging from about 50° C. to about 200° C. and step (c) is carried out at a temperature ranging from about −10° C. to about 100° C.

3. The process of claim 2 wherein step (a) is carried out at a temperature ranging from about 25° C. to about 130° C., step (b) is carried out a temperature ranging from about 75° C. to about 175° C. and step (c) is carried out at a temperature ranging from about 0° C. to about 80° C.

4. The process of any one of claims 1-3 wherein the alkali metal catalyst comprises sodium or potassium deposited on calcium oxide or aluminum oxide, the isomerization catalyst comprises a porous alumina promoted by potassium carbonate and the disproportionation catalyst comprises rhenium oxide supported on alumina.

5. The process of claim 4 wherein the disproportionation catalyst is promoted with tetraalkyl tin.

6. The process of claim 5 wherein the tetraalkyl tin is selected from tetramethyl tin, tetraethyl tin, tetrapropyl tin, tetrabutyl tin and mixtures thereof.

7. The process of claim 6 wherein the tetraalkyl tin is tetrabutyl tin.

* * * * *